US012571811B2

(12) United States Patent
Tjandra et al.

(10) Patent No.:  US 12,571,811 B2
(45) Date of Patent:  Mar. 10, 2026

(54) SYSTEMS AND PROCESSES FOR IMAGE-BASED SAMPLE IDENTIFICATION, MONITORING, AND ASSESSMENT

(71) Applicant: NERv Technology Inc., Kitchener (CA)

(72) Inventors: Ricky Tjandra, Kitchener (CA); Abdallah Hassen El-Falou, Kitchener (CA)

(73) Assignee: NERv Technology Inc., Kitchener (CA)

( * ) Notice: Subject to any disclaimer, the term of this patent is extended or adjusted under 35 U.S.C. 154(b) by 0 days.

(21) Appl. No.: 18/431,048

(22) Filed: Feb. 2, 2024

(65) Prior Publication Data

US 2024/0264185 A1      Aug. 8, 2024

Related U.S. Application Data

(60) Provisional application No. 63/482,923, filed on Feb. 2, 2023.

(51) Int. Cl.
    *G16H 50/30*      (2018.01)
    *G01N 35/00*      (2006.01)
    *H04N 7/18*       (2006.01)
(52) U.S. Cl.
    CPC ....... *G01N 35/00722* (2013.01); *G16H 50/30* (2018.01); *H04N 7/18* (2013.01)
(58) Field of Classification Search
    CPC .............. G11B 27/031; G06F 3/04845; G06F 3/04847
    See application file for complete search history.

(56) References Cited

U.S. PATENT DOCUMENTS

| 8,145,431 | B2 | 3/2012 | Kloepfer et al. |
| 8,591,836 | B2 | 11/2013 | Young et al. |
| 8,947,656 | B2 | 2/2015 | Cunningham |
| 9,311,520 | B2 | 4/2016 | Burg et al. |
| 9,445,749 | B2 | 9/2016 | Erickson et al. |
| 10,753,861 | B2 | 8/2020 | Zaccari et al. |
| 11,158,420 | B2 | 10/2021 | Adiri et al. |
| 11,193,892 | B2 | 12/2021 | Clarke et al. |

(Continued)

FOREIGN PATENT DOCUMENTS

WO          2015157691 A1    10/2015

*Primary Examiner* — Thai Q Tran
*Assistant Examiner* — Jose M Mesa
(74) *Attorney, Agent, or Firm* — Stratford Group Ltd.

(57)          ABSTRACT

Disclosed herein are systems and processes for image-based sample monitoring and patient risk assessment. The system preferably comprises a sample receiving surface comprising a sample well and a plurality of calibration markings, an image capturing device, configured to capture an image of the sample receiving surface, and a processing unit, configured to receive the image from the image capturing device, and convert the image to usable data. The process preferably comprises transferring a sample to the sample well, capturing an image of said sample receiving surface with an image capturing device, sending the image to a processing unit, processing, with the processing unit, said image to obtain usable data, and saving, with a memory unit, the usable data. Usable data may be analyzed and shared with health care providers or with a database of sample data for sorting and classifying the data.

20 Claims, 7 Drawing Sheets

(56) References Cited

U.S. PATENT DOCUMENTS

| | | | |
|---|---|---|---|
| 2012/0201437 A1* | 8/2012 | Ohnemus | G16B 35/00 |
| | | | 382/128 |
| 2017/0000407 A1 | 1/2017 | Saxby et al. | |
| 2019/0277831 A1* | 9/2019 | Johnson | A61B 5/150022 |
| 2019/0302008 A1 | 10/2019 | Ohta et al. | |
| 2022/0026275 A1 | 1/2022 | Asghar et al. | |
| 2022/0130493 A1* | 4/2022 | Turner | G16H 70/40 |

* cited by examiner

SYSTEMS AND PROCESSES FOR IMAGE-BASED SAMPLE IDENTIFICATION, MONITORING, AND ASSESSMENT

CROSS-REFERENCE TO RELATED PATENT APPLICATIONS

This application claims priority from U.S. Provisional Patent Application No. 63/482,923, filed on Feb. 2, 2023, the disclosure of which is hereby incorporated herein in its entirety by reference.

FIELD OF THE DISCLOSURE

The present disclosure relates generally to the field of colour monitoring, and more specifically to systems and processes for image-based sample identification, monitoring, and assessment.

BACKGROUND

Surgical procedures may use open and minimally invasive techniques on users, such as patients, in order to identify and treat pathological conditions or improve body functions. Surgeries performed due to a variety of reasons have an inherent risk of post-operative complications such as hemorrhages, infections and leakages to develop.

Post surgical complications may comprise, without limitation, post-operative leakages, ischemia, infection, and sepsis.

One of the most dangerous complications for surgery is a complication known as anastomotic leakage. Anastomotic leakage may develop after an anastomosis is performed where two organs are surgically connected, and is most commonly observed in gastrointestinal surgery. Anastomotic leakage leads to luminal contents leaking into the peritoneal cavity which may cause a cascade of deadly complications to arise. This typically involves a form of severe sepsis, peritonitis, morbidity and it may lead to mortality.

In order to estimate post operative risk for a patient, healthcare providers may rely on various methods of analyzing patient data following a surgery.

Traditional diagnostic techniques include waiting for clinical factors such as abdominal pain, fever and tachycardia to arise. Consequently, it can take three to seven days on average for a leak to be diagnosed. This is very dangerous, especially considering that every hour of delay causes a considerable increase in the morbidity and mortality risk for the patient.

Imaging techniques such as Computed Tomography (CT) imaging can be used for leakage detection, however, CT imaging has certain drawbacks, especially due to its low sensitivity, ionizing radiation and the long time it takes to acquire and assess an image. Such systems and technologies require hospital facilities and trained personnel from different specialty teams in order to operate these technologies.

Any discussion of the related art throughout the specification should in no way be considered as an admission that such related art is widely known or forms part of common general knowledge in the field.

U.S. Pat. No. 9,445,749 discloses a smartphone-based apparatus and method for obtaining repeatable, quantitative colorimetric measurements. The device includes a reactive test platform, with the sample surface directly attached to a smartphone camera for controlling the light of an image taken by the smartphone. Diagnostics are based on quantitative values.

U.S. Pat. No. 8,145,431 discloses a body fluid testing component for simultaneous analyte detection. This testing component has a reactive test platform, and diagnostics are based on quantitative values.

U.S. Pat. No. 931,152 discloses a method and apparatus for performing and quantifying color changes induced by specific concentrations of biological analytes in an automatically calibrated environment. A reactive test platform is measured.

US20170000407 discloses systems and methods for wound monitoring based on measuring the colour of a pH indicator.

U.S. Pat. No. 11,158,420 discloses tracking wound healing progress using remote image analysis. This is a method for analyzing the colour of a wound, which does not provide any quantitative data. Further, the method is not applicable to fluids or biofluids without a reactive test platform.

U.S. Pat. No. 8,947,656 discloses a smartphone biosensor, which includes an optical reactive platform such as a crystal, or additional light dispersion methods for spectroscopic methods.

U.S. Pat. No. 10,753,861 discloses methods for colorimetric analysis. The method includes determining the presence or concentration of an analyte in a sample. Determining the presence or concentration of an analyte in a sample includes receiving a first image containing an image of the sample, the first image obtained using an image sensor having two or more colour channels. The method requires a pretreated lateral flow test strip.

US20220026275 discloses systems and methods for detecting disease using a mobile device. The method requires a reactive test platform in the form of a lateral flow test strip which has been pretreated.

U.S. Pat. No. 11,193,892 discloses methods and devices for measuring the levels of analytes in body fluids. This is a targeted analytical method which requires a reactive test platform.

All documents cited herein are incorporated by reference.

There is a need in the art for a non-invasive colour monitoring system and process that directly captures and analyses a sample's colour for providing a diagnostic assessment.

There is also a need in the art for a simple colour monitoring system and process that does not require any reactive test platform or colorimetric reaction analysis.

None of the above cited documents, alone or in combination satisfy the need for a simple smart phone operated colour monitoring system and process that directly captures and analyzes a sample colour to provide a diagnostic assessment.

BRIEF SUMMARY

It is an object of the disclosure to provide systems and processes for image-based sample identification, monitoring, and assessment.

In accordance with an aspect of the disclosure there is provided a system for monitoring a sample, the system comprising: a sample receiving surface comprising a sample well for receiving sample and a plurality of calibration markings; an image capturing device, configured to capture an image of said sample receiving surface; and a processing unit, said processing unit configured to receive said image from said image capturing device, and convert said image to usable data.

In accordance with an embodiment of the disclosure the system further comprises: a memory unit, configured to save said usable data; a display element, said display element being configured to display said usable data.

In accordance with an embodiment of the disclosure, the usable data comprises one or more of: colorimetric data, spectrophotometric data, turbidity data, dynamic light scattering data, particle size estimation, particle counting, sample volume, fluorescence, phosphorescence, and reflectance data.

In accordance with an embodiment of the disclosure, the system further comprises a sorting unit, said sorting unit configured to receive said usable data from said processing unit, and convert said usable data into sorted data.

In accordance with an embodiment of the disclosure, the sorting unit further comprising a database comprises a plurality of sample data and time-dependent data, wherein the sorted data is classified based on its comparison to the database.

In accordance with an embodiment of the disclosure, the sorting unit further comprises one or more of: a machine learning algorithm, control charts, trends, and calibration curves.

In accordance with an embodiment of the disclosure, the sample is a biofluid, comprising one or more of: saliva, blood, urine, drainage fluid, plasma, wound drainage, cerebrospinal fluid, and sweat.

In accordance with an embodiment of the disclosure, the image capturing device comprises a smartphone, or camera.

In accordance with an embodiment of the disclosure, the image capturing device continuously captures a plurality of images of said sample receiving surface; and the usable data comprises time-dependent data.

In accordance with an embodiment of the disclosure, the system further comprises an enclosure, the enclosure configured to shield the sample receiving surface from external light and contaminants.

In accordance with an aspect of the disclosure there is provided a process for image-based sample monitoring and patient risk assessment, the process comprising: capturing, with an image capturing device, an image of a sample well and a plurality of calibration marking, the sample well and the plurality of calibration markings positioned on a sample receiving surface; sending said image to a processing unit; processing, with said processing unit, said image to obtain usable data.

In accordance with an embodiment of the disclosure, the process further comprises: saving said usable data to a memory unit; and displaying said usable data on a display element.

In accordance with an embodiment of the disclosure, the process further comprises: saving said usable data to a memory unit; and displaying said usable data on a display element.

In accordance with an embodiment of the disclosure, said usable data comprises one or more of: colorimetric data, spectrophotometric data, turbidity data, dynamic light scattering data, particle size estimation, particle counting, sample volume, fluorescence, phosphorescence, and reflectance data.

In accordance with an embodiment of the disclosure, the process further comprises a sorting unit, said sorting unit configured to receive said usable data from said processing unit, and convert said usable data into sorted data.

In accordance with an embodiment of the disclosure, the sorting unit further comprises one or more of: a machine learning algorithm, control charts, trends, and calibration curves.

In accordance with an embodiment of the disclosure, the sorting unit further comprises a database comprising a plurality of sample data and time-dependent data, wherein the sorted data is classified based on its comparison to the database.

In accordance with an embodiment of the disclosure, the sample is a biofluid, comprising one or more of: saliva, blood, urine, drainage fluid, plasma, wound drainage, cerebrospinal fluid, and sweat.

In accordance with an embodiment of the disclosure, the image capturing device comprises a smartphone or camera.

In accordance with an embodiment of the disclosure, the image capturing device continuously captures a plurality of images of said sample receiving surface; and the usable data comprises time-dependent data.

In accordance with an embodiment of the disclosure, the sample well comprises an enclosure, the enclosure configured to shield the sample receiving surface from external light and contaminants.

The advantages and features of the present disclosure will become better understood with reference to the following more detailed description and claims taken in conjunction with the accompanying drawings in which like elements are identified with like symbols.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

In the figures, embodiments are illustrated by way of example. It is to be expressly understood that the description and figures are only for the purpose of illustration and as an aid to understanding.

Figure 1:
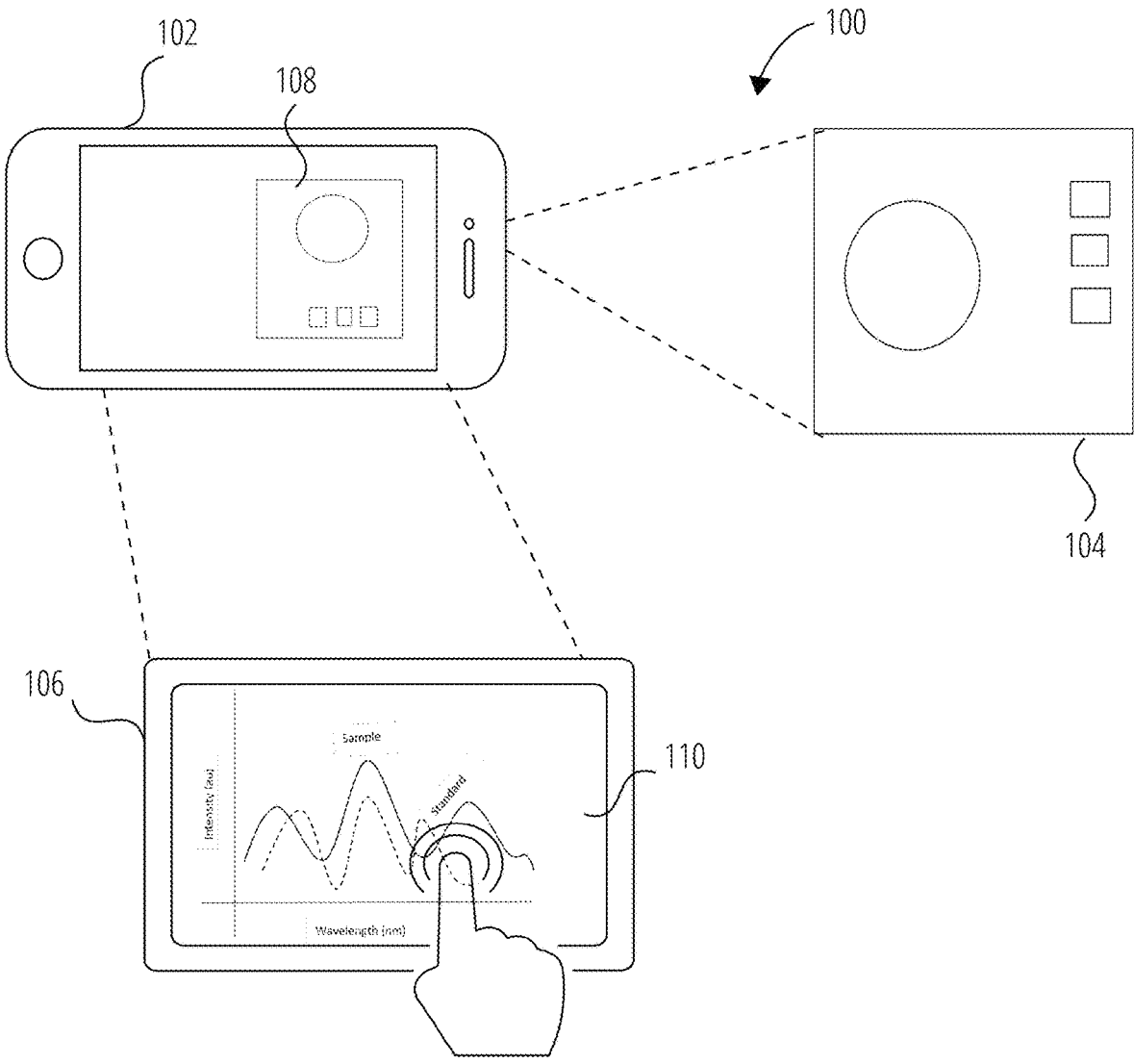
Figure 2:
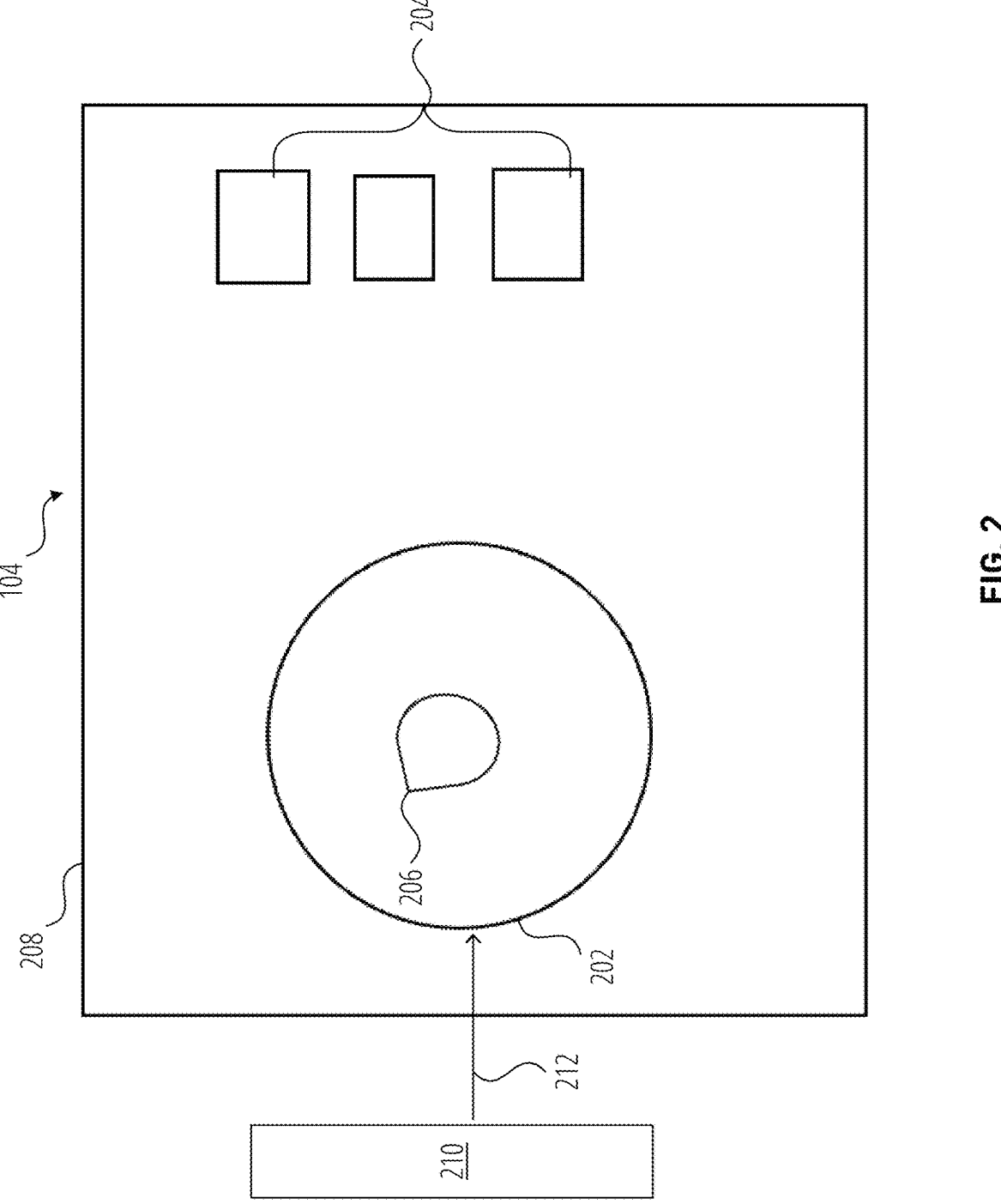
Figure 3:
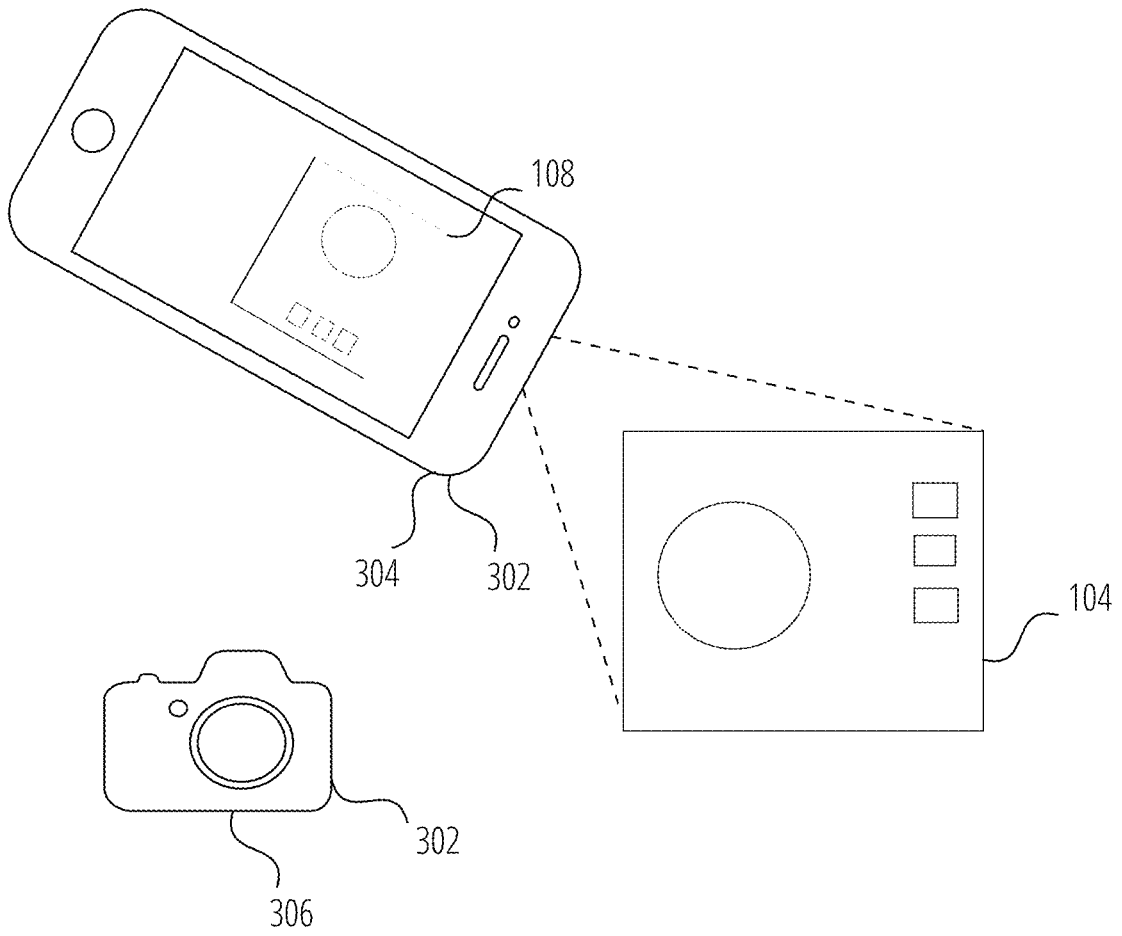
Figure 4:
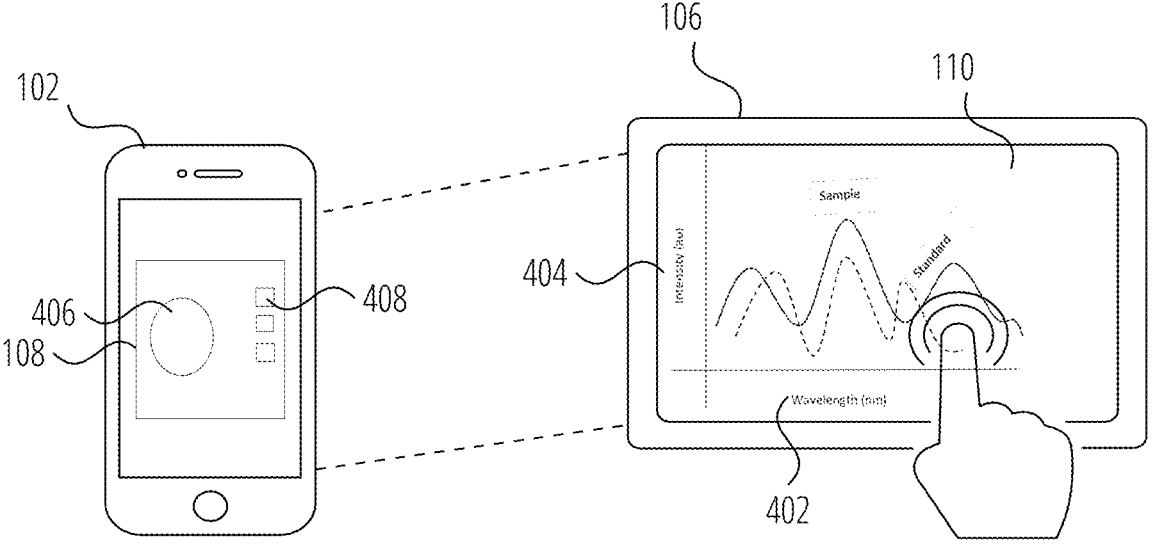
Figure 5:
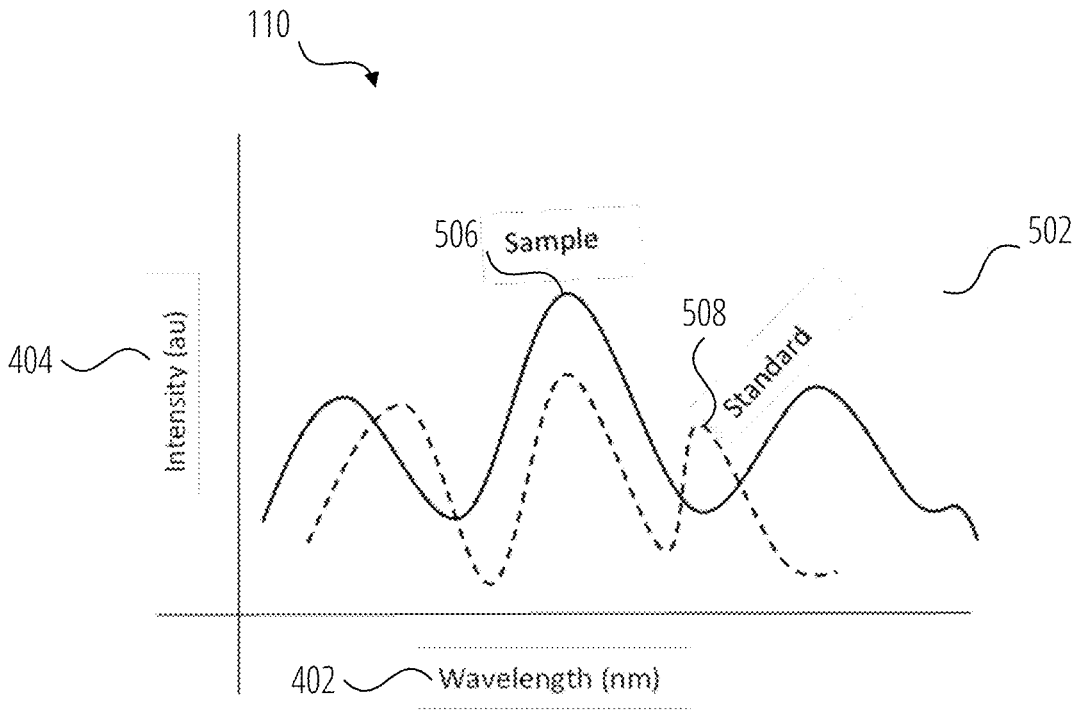
Figure 5:
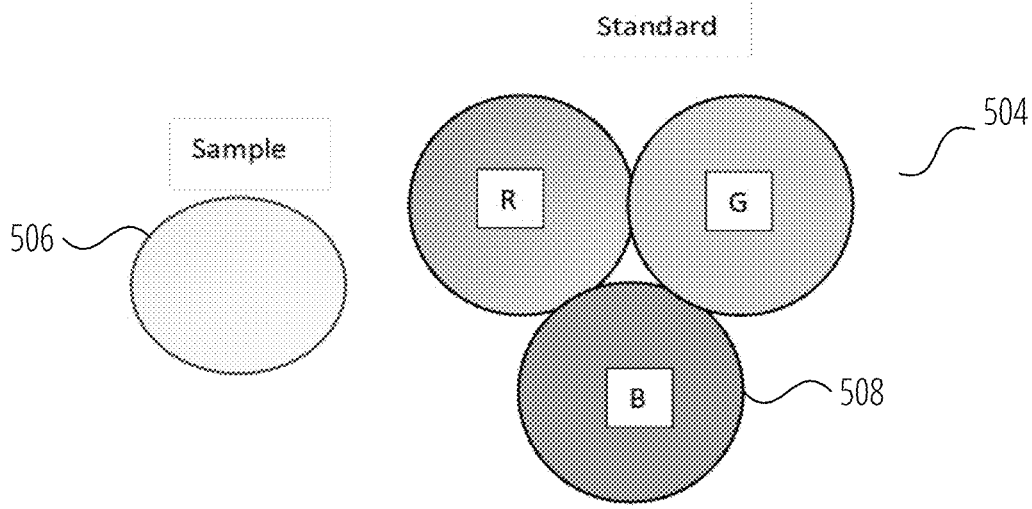
Figure 6A:
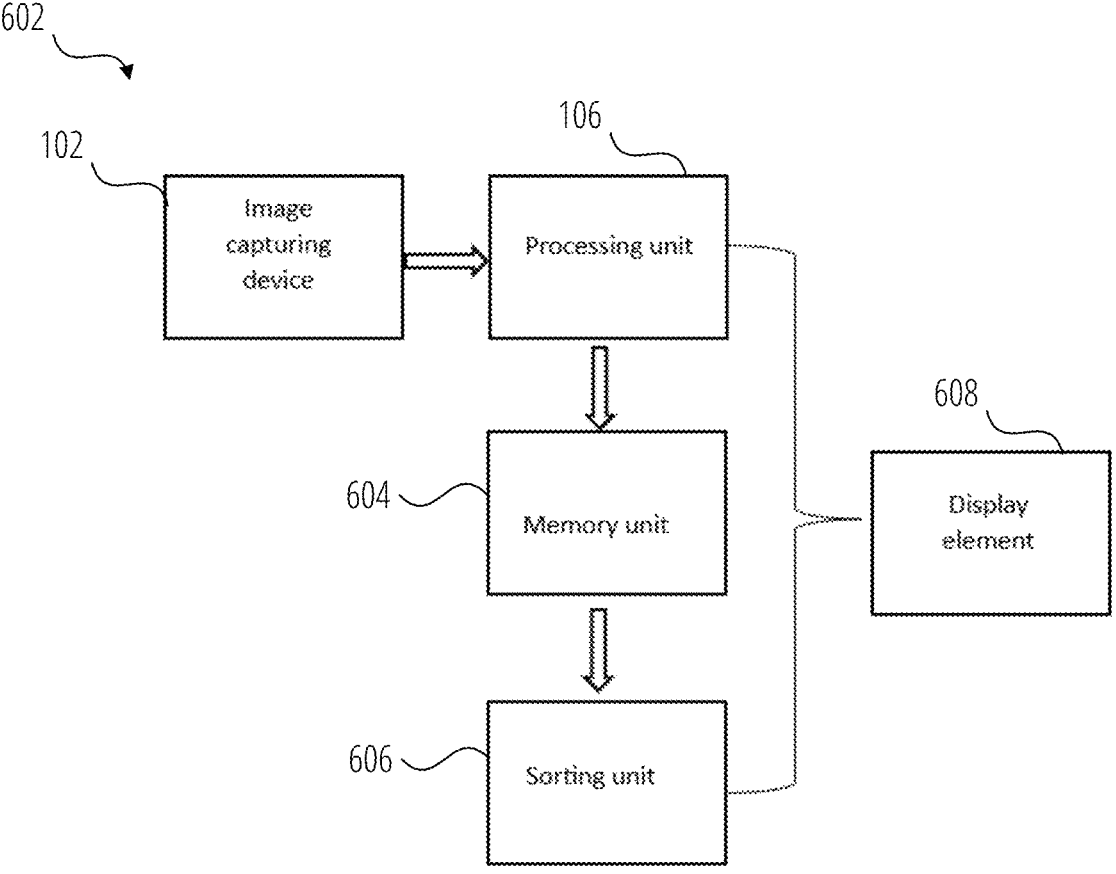
Figure 6B:
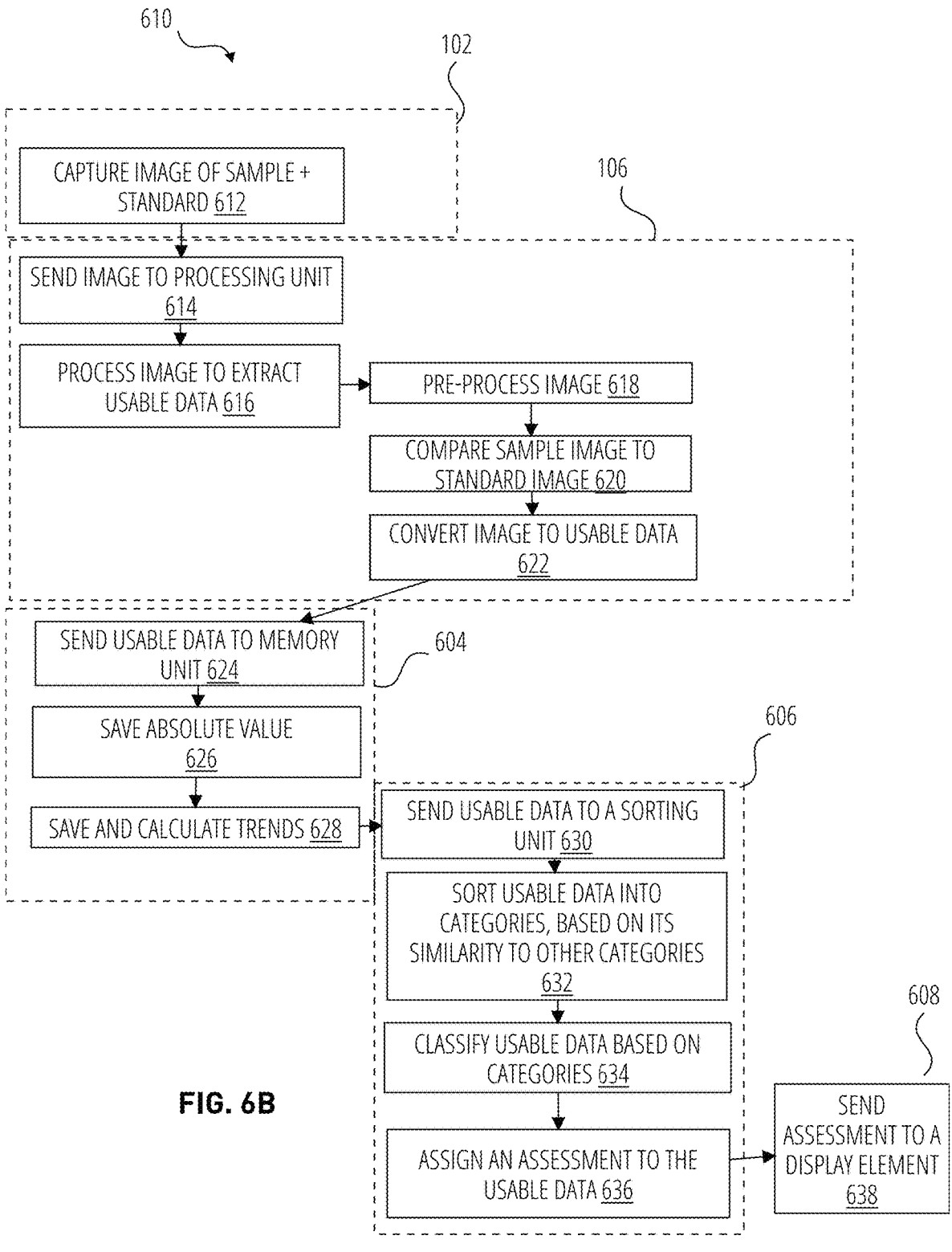

Embodiments will now be described, by way of example only, with reference to the attached figures, wherein the figures:

FIG. 1 illustrates a representation of a system for monitoring a sample, in accordance with one embodiment;

FIG. 2 illustrates a top view of a sample receiving surface, in accordance with one embodiment;

FIG. 3 illustrates a representation of a system for monitoring a sample, in accordance with one embodiment;

FIG. 4 illustrates a representation of a system for monitoring a sample, in accordance with one embodiment;

FIG. 5 illustrates an example of processing data, in accordance with one embodiment;

FIG. 6A illustrates a process for image-based monitoring of a sample, in accordance with one embodiment; and FIG. 6B illustrates a process for image-based monitoring of a sample, in accordance with one embodiment.

DETAILED DESCRIPTION

Systems and methods for carrying out the disclosure are presented in terms of embodiments depicted within the FIGS. However, the disclosure is not limited to the described embodiments, and a person skilled in the art will appreciate that many other embodiments of the disclosure are possible without deviating from the basic concept of the disclosure, and that any such work around will also fall under scope of this disclosure. It is envisioned that other styles and configurations of the present disclosure can be easily incorporated into the teachings of the present disclosure, and the configurations shall be shown and described for purposes of clarity and disclosure and not by way of limitation of scope.

The features of the disclosure which are believed to be novel are particularly pointed out in the specification. The present disclosure now will be described more fully hereinafter with reference to the accompanying drawings, which are intended to be read in conjunction with both this summary, the detailed description and any preferred and/or particular embodiments specifically discussed or otherwise disclosed. This disclosure may however, be embodied in many different forms and should not be construed as limited to the embodiments set forth herein; rather, these embodiments are provided by way of illustration only and so that this disclosure will be thorough, complete and will fully convey the full scope of the disclosure to those skilled in the art.

FIG. 1 illustrates a system for monitoring a sample 100, the system comprising a sample receiving surface 104, an image capturing device 102, and a processing unit 106.

The image capturing device 102 is preferably configured to capture an image 108 of said sample receiving surface 104.

The processing unit 106 is preferably configured to receive the image 108 from the image capturing device 102 and convert the image to usable data 110.

Usable data 110 may comprise one or more of: colorimetric data, spectrophotometric data, turbidity data, dynamic light scattering data, particle size estimation, particle counting, sample volume, fluorescence, phosphorescence, and reflectance data (described in more detail in FIG. 5). Usable data 110 may comprise a time-stamp associated with an image, such that the processing unit 106 may derive time-dependent trends in usable data 110 obtained from a plurality of images 108, taken over a certain time period.

FIG. 2 illustrates an aspect of a system for monitoring a sample 100.

The sample receiving surface 104 preferably comprises a sample well 202, for receiving a sample 206, and a plurality of calibration markings 204, for providing standard colour. measurements, comparable to the sample colour.

The sample receiving surface 104 may be a simple flat surface of plastic, glass, or similar.

Alternatively, the sample receiving surface 104 may be coupled with a microfluidics device 210 or system, which may receive the sample 206 from the patient, automatically or manually, prior to flowing the sample 206 to the sample receiving surface 104 by means of a fluidic connection 212, such as a fluid channel, or manual or automatic pipetting.

In an example of an embodiment, the microfluidic system may comprise passive or non-passive sampling or sample preparation techniques, which may include, but are not limited to, filtering, refining, adding reagents to, the sample 206. The prepared sample 206 may then flow to the sample well 202 for image capturing.

The sample well 202 preferably receives a sample 206, automatically, by flowing sample from a patient, or through an automatic sample device, or manually, from a healthcare professional or the patient. Samples 206 may preferably, but need not necessarily, be fluids. Samples may be taken manually from a patient, for example by a healthcare professional or by the patient themselves, and disposed on the sample receiving surface 104.

A fluid sample 206 may flow through a diffusion material, in order to filter the sample and flow it through to the sample well 202, through capillary action. Diffusion materials may comprise nitrocellulose membranes or similar, microfluidic channels-either active or passive, or other materials known in the art. Microfluidic channels may comprise polymeric material or similar.

Samples and/or standards may be colorimetrically tagged in order to detect sensitive molecules (such as enzymes, aptamers, and the like), from an image of the sample 206.

Samples may flow to the sample well 202 and exhibit a colour on the sample well, via a lateral flow assay (LFA), or other chromatographic separation techniques known in the art.

While prior art LFAs such as pregnancy tests or COVID tests may be capable of indicating whether or not an analyte is present, coupling this qualitative test platform with the image capturing device 102 and its processing unit 106 has the added benefit of capturing quantitative aspects of the sample well 202, including, but not limited to, the intensity of samples vs. standards, distance traveled (based on polarity, size, hydrodynamic radius, of analyte/sample strip), and the like, all of which may be input by the processing unit 106 into some computer implemented sorting unit 606 (described in more detail in FIG. 6), in order to identify the analyte, or provide a quantitative assessment of the amount of analyte present in the sample 206.

Samples 206 and the plurality of calibration markings 204, may be stimulated by light or heat, while taking a picture in order to identify specific biomarkers, such as fluorescent biomarkers.

In an alternate embodiment, samples 206 may be solid, for example for monitoring wound colour. In an alternate embodiment, samples 206 may be gaseous or vapour.

Fluid samples may preferably, but need not necessarily, comprise biofluid samples, such as saliva, blood, urine, drainage fluid, plasma, wound drainage, cerebrospinal fluid, and sweat, and the like.

Biofluids may be sampled from, for example, a drain, catheter, arterial line, an evacuator, and the like, and placed onto the sample well 202 on the sample receiving surface 104.

A drain may comprise peritoneal drains, pleural drains, cranial drains, and the like.

The plurality of calibration markings 204 typically corresponds with known or standard colour values, for comparison with a sample 206.

In one embodiment, the plurality of calibration markings 204 are on the same substrate or surface as the sample well 202, so that when an image is taken of the sample receiving surface 104, it may capture the sample well 202 with the sample 206 and the plurality of calibration markings 204 under the same lighting conditions, which minimizes error and/or processing steps.

In an alternate embodiment, the plurality of calibration markings 204 may be separate from the sample well 202. For example, the plurality of calibration markings 204 may be in the form of a card(s)/sticker(s) and the like with known color values. It may be integral to the sample receiving surface 104 or removable from it.

Samples 206 may be analyzed directly from a patient, for example from drains/catheters, without removing an aliquot for a picture. The plurality of calibration markings 204 may be disposed (as a sticker, for example), on a transluscent or transparent fluid line, catheter, or drain, such that an image capturing the fluid line captures comparative colours for making an assessment or diagnosis, without taking a sample.

The sample receiving surface 104 can be made out of glass, polymers or various other materials.

There may be included an enclosure 208, such as a box, lid, or the like, for enclosing the sample receiving surface

104, to limit potential light leakage and/or to make lighting conditions consistent. In some embodiments, the enclosure may form a seal around the sample receiving surface 104, keeping out light and/or contaminants. The enclosure may contain the image capturing device 102, or provide a transparent, covered surface on which the image capturing device 102 may rest in order to capture an image 108. Alternatively, the enclosure 208 may be attachable to the image capturing device 102, and may seal around the sample well 202. The enclosure 208 or the image capturing device 102 may be equipped with light filters or flashes, which may be triggered while capturing an image, control the light that the sample 206 and the plurality of calibration markings 204 are exposed to.

FIG. 3 illustrates an image capturing device 102 capturing an image 108 of a sample receiving surface 104.

The image capturing device 102 may comprise a smartphone 304, a camera 306, or similar.

A smartphone, regardless of its platform (i.e. android, iphone) may comprise a camera and a flash, which can act as a sensor and light source, respectively.

Alternatively, a higher resolution sensor and/or light source may be coupled to the image capturing device 102 in order to improve the quality of the image 108 taken by the image capturing device 102.

An image 108 of the accessory is preferably taken using the image capturing device 102, the image preferably being in a raw image format (RAW) or another similar, lossless format.

The image capturing device 102 may be equipped with a filter unit, which may be configured to filter out one or more colours, wavelengths, or intensities, from the captured image 108.

For example, the image capturing device 102 may be equipped with an infrared (IR) filter, for filtering out all wavelengths of light that are not in a range corresponding with IR light (780 nm to 1 mm).

A camera flash, either an external flash or a flash that is integral to the image capturing device 102, may or may not be used to illuminate the sample receiving surface 104.

FIG. 4 illustrates a processing unit 106, which is preferably configured to receive the image 108 from the image capturing device 102, and convert the image 108 to usable data 110.

The processing unit 106 converts the image 108, by comparing the sample image 406 to the standard image 408 markings, to produce usable data 110.

Processing of the image may comprise pre-processing steps, which may include cropping, boundary identification, white balance, and other corrections based on calibration mark values, artifact, and noise removal.

Pre-processing steps may also include a calibration step, wherein the plurality of calibration markings 204 may be compared with known color standards, in order to correct individual differences between image capturing devices 102 hardware and software, as well as ambient lighting conditions.

In the illustrated embodiment, the usable data 110 can be visualized as wavelength data 402 and intensity data 404.

The image capturing device 102 may be equipped with the processing unit 106 for processing the image.

For example, but not by way of limitation, the smartphone 304 may be equipped with an application which processes the image.

Alternatively, the image 108 may be taken with a camera or smartphone and uploaded to a computer, the computer being equipped with the processing unit 106.

The image 108 may be uploaded by way of a physical connection, such as a cable or remotely, via an internet connection, Bluetooth, near-field communication (NFC), or similar.

FIG. 5 illustrates two examples of usable data 110.

The usable data 110 may comprise spectrophotometric data 502, which may include wavelength data 402 and intensity data 404.

In another embodiment, usable data 110 may comprise colorimetric data 504, for example in a colour space: red, green, blue (RGB); cyan, magenta, yellow, and key (CMYK); hue, saturation, and lightness (HSL); and hue, saturation, and value/brightness (HSV/HSB).

Usable data 110 may be used to quantify fluorescence of a sample.

Usable data 110 may also comprise turbidity data, dynamic light scattering data, particle size estimation, particle counting, sample volume, reflectance and the like.

The processing unit 106 may convert an image to usable data 110 by comparing sample data 506 to standard data 508.

FIG. 6A illustrates a system for image-based sample monitoring and risk assessment 602, comprising an image capturing device 102 and a processing unit. Optional additional elements may include a memory unit 604, a sorting unit 606, and a display element 608.

A memory unit 604 may comprise, for example, a hard drive, a USB, or some other means of saving usable data 110. A sorting unit may comprise a machine learning algorithm, control charts, trends, calibration curves, and the like, which may compare known qualities of bioanalytes, stored in the memory unit 604, with the qualities of the sample 206 obtained by processing usable data 110.

FIG. 6B illustrates a process for image-based monitoring and risk assessment of a sample 610 is illustrated. The process comprises:

1. Capturing, with the image capturing device 102, an image of a sample and a standard 612;

2. Send the image to a processing unit 106 614;

3. Process the image with the processing unit 106 to obtain usable data 616;

a. Pre-process the image (optional) 618;

b. Compare the sample image to the standard image 620;

c. Convert the image to usable data 622;

d. Send usable data to a memory unit 604 624;

i. Save absolute value 626;

ii. Save and calculate trends 628;

iii. Send usable data to a sorting unit 630;

1. Sort usable data into categories, based on its similarity to other categories 632;

2. Classify usable data based on categories 634;

3. Assign an assessment to usable data;

4. Send assessment to a display element 608 for displaying the assessment.

Images may be taken continuously and/or automatically, for example every 15 minutes. The processing unit 106 converts the image into usable data 110, which may have a time-stamp. In such an embodiment, the sorting unit 606 may classify and assess usable data based on known trends in the data.

It can be seen from the process 610, usable data may be used in a variety of different ways to provide an assessment of a sample.

An assessment may be in the form of a risk value such as high risk or low risk. It could alternatively be a diagnostic assessment, such as an indication of an analyte being present or not present in the sample.

When processed, the usable data may be available as an absolute value, for example a colour value or wavelength value.

An assessment may be provided based on the absolute value, and then sent to a display element 608, such as a digital screen, physical read-out, or similar, to be displayed.

In an embodiment, quantitative assessments may be provided by the sorting unit 606, which may comprise reporting a concentration of a bioanalyte, derived from the usable data 110 obtained from the image 108. A quantitative assessment may be taken to assign a risk value to a the patient that the sample 206 was obtained from-i.e. a notification that a biomarker is low, and a given risk associated with the low concentration of the biomarker.

In another embodiment, qualitative assessments may be provided, which may comprise relative, positive/negative ("yes/no"), assessments of the patients' condition. For example, if urine is being monitored for its colour, and its colour is expected to be yellow, a risk value of "high" may be assigned if a colour other than yellow is present in an image of the sample. In the same vein, if the image of the sample comprises only yellow, a risk value of "low" may be assigned. Similarly, a sample may be analyzed for the presence of a biomarker, such as a fluorescent biomarker. If the biomarker is found to be present or not present in the sample, a diagnostic value of "present" or "not present" may be assigned.

The assessment can then be sent to the display element 608 so that a user, for example a healthcare provider, may view the assessment.

It may be preferable to keep track of the usable data. The process 610 may comprise sending the usable data to a memory unit 604, for saving and analyzing the usable data.

The memory unit 604 may be used to develop an Electronic Medical Record (EMR) and/or an Electronic Health Record (EHR) of a patient, which can be sent, automatically, in real-time (live), or manually, to a medical care provider such as doctor. Alternatively, or in combination, a patient's existing EMR may be sent to the memory unit 604 and integrated with the sample data 506 to form a more comprehensive assessment of the patient.

The EMR or EHR may aid a medical care provider in clinical decision making, diagnosing diseases, and assessing risk. Trends in the values of the usable data may be analyzed to assign a risk value to a sample. For example, a patient's urine may be analyzed for hydration of the patient by plotting colour against time. A risk value may be assigned depending on a slope of a plot, its intercept, and the like.

Any data obtained from the image may be plotted against time for determining trends in a patient's condition. For example, wound colour vs. time may be plotted for assessing wound healing. Sample volume vs. time may be plotted for plethysmography analysis, including photoplethysmography, wherein blood volume changes may be measured and/or evaluated for evaluating cardiac conditions, respiratory conditions, and the like.

Similarly, photopethysmography may comprise obtaining a video of a patient's face to analyze colour changes in the patient's skin.

Analysis based on historical values may be sent to the display element 608 for displaying trends and risk/diagnostic values. A quantitative readout of a biofluid's colour may be displayed and compared against known values and previous values, if available, to detect changes of composition in the biofluids. An assessment of a patient's vitals may be determined and displayed from the usable data and/or trends in the usable data.

Alternatively, or perhaps in combination with the above mentioned uses, the usable data may be sent to a sorting unit 606, to be sorted or classified, whether it be based on an absolute value of usable data, or based on its relation to other fluid types.

The sorting unit 606 may be, for example a machine learning algorithm, a control chart, a plot of fluid colour vs. time, or similar.

The usable data may be entered into a sorting unit to be sorted or classified into various sample types.

For example, a fluid colour may be entered into a machine learning algorithm to classify its fluid type based on its colour value. For example, a fluid may be classified as "blood" if it comprises similar characteristics to other fluids that had been classified as blood, such as having a red colour. A fluid colour may be entered into a machine learning algorithm to classify or identify mixtures of fluids.

Generally, the computer components, referred to as "units" or "engines" may be communicatively coupled by any means known in the art, including wireless and wired connections. The processor may send data to the memory and/or to the sorting unit, and the memory may send data to the sorting unit. The sorting unit may access data stored in the memory pertaining to a plurality of other patients, in order to classify the data obtained from the patient providing the sample at the time of the process 610.

Additionally, and/or in combination with a machine learning algorithm, the usable data 110 may be entered into a remotely connected database, such as a Cloud database, where a plurality of sample data and time-dependent sample data may be stored, which may act as the sorting unit 606, in order to classify the usable data.

The remotely connected database may preferably, but need not necessarily, comprise a variety of sample data from a plurality of patients, said sample data being sorted and classified into categories, the categories being applied to sorting and classifying the usable data.

For example, the colour of the sample fluid may be compared to a Cloud database comprising a variety of fluids that have been sorted into fluid types, based on their colour, and then the sample fluid may be assigned a fluid type. Usable data may be added to the database to further improve predictions and classifications.

Alternative embodiments of the present disclosure may additionally, but need not necessarily, comprise reactive test platforms on the sample well 202.

Reactive test platforms may react with the sample 206 to produce a physical change or chemical response, such as colorimetric changes, phosphorescence responses, reflectivity fluorescence responses, chromatographic changes, and the like.

In some embodiments, different machine-learning algorithms or techniques may be used, alone or in combination, in the different functional units noted above.

These may include, for example, deep learning architectures such as Deep Belief Network (DBN), Stacked Auto Encoder (SAE), Convolutional Neural Network (CNN) or Recurrent Neural Network (RNN) may be used. Other examples include, without limitation, Restricted Boltzmann machines (RBM), Social Restricted Boltzmann Machines (SRBM), Fuzzy Restricted Boltzmann Machines (FRBM), TTRBM models of Deep Belief Networks (DBN) or similar approaches could be used; AE, FAE, GAE, DAE, BAE models of Statistically Adjusted End Use (SAE) models could be used; models such as AlexNet, ResNet, Inception, VGG16, ECNN models of CNN may be used; Bidirectional Recurrent Neural Networks (BiRNN), Long Short-Term Memory (LSTM) networks, Gate Recurrent Unit (GRU) of RNN may also be used. Additional techniques specific to time-series modelling may be used, including, but not limited to, dynamic time warping, change point detection, and ARIMA.

In some embodiments, other types of algorithms such as physics-based mathematical computations and basic multiple linear regression models may also be relied upon in conjunction with or in complementarity with those architectures and learning algorithms.

Many of the functional units described in this specification have been labeled as "engines", or "units" in order to more particularly emphasize their implementation independence. For example, an engine or unit may be implemented as a hardware circuit comprising custom VLSI circuits or gate arrays, off-the-shelf semiconductors such as logic chips, transistors, or other discrete components. An engine may also be implemented in programmable hardware devices such as field programmable gate arrays, programmable array logic, programmable logic devices or the like.

Engines or units may also be implemented in software for execution by various types of processors. An identified engine or unit of executable code may for instance, comprise one or more physical or logical blocks of computer instructions which may for instance, be organized as an object, procedure, or function. Nevertheless, the executables of an identified engine need not be physically located together, but may comprise disparate instructions stored in different locations which, when joined logically together, comprise the engine and achieve the stated purpose for the module.

Indeed, an engine of executable code may be a single instruction, or many instructions, and may even be distributed over several different code segments, among different programs, and across several memory devices. Similarly, operational data may be identified and illustrated herein within engines, and may be embodied in any suitable form and organized within any suitable type of data structure. The operational data may be collected as a single data set, or may be distributed over different locations including over different storage devices, and may exist, at least partially, merely as electronic signals on a system or network. Where an engine or portions of an engine are implemented in software, the software portions are stored on one or more computer readable storage media.

It should be understood that the models described herein may be trained using various sources of data. Alternative methods of assembling predictions from individual models may be employed (for example, passing into a Logistic Regression model instead of using thresholds for classification).

Systems and methods described herein may further comprise features such as a prompt to request inputs of additional data at key times to update a model or risk assessment. For example, a prompt for an image of drainage fluid at post-operative hour 6, which can be used to update a risk assessment.

The sorting methods disclosed herein can be deployed in firmware or cloud and updated/improved as needed. They can be further adapted to detect different types of post operative complications.

The present disclosure includes systems having processors to provide various functionality to process information, and to determine results based on inputs. Generally, the processing may be achieved with a combination of hardware and software elements. The hardware aspects may include combinations of operatively coupled hardware components including microprocessors, logical circuitry, communication/networking ports, digital filters, memory, or logical circuitry. The processors may be adapted to perform operations specified by a computer-executable code, which may be stored on a computer readable medium.

The steps of the methods described herein may be achieved via an appropriate programmable processing device or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the exemplary embodiments discussed above and appreciated by those skilled in the computer and software arts. Appropriate software can be readily prepared by programmers of ordinary skill based on the teachings of the exemplary embodiments, as is appreciated by those skilled in the software arts. In addition, the devices and subsystems of the exemplary embodiments can be implemented by the preparation of application-specific integrated circuits, as is appreciated by those skilled in the electrical arts. Thus, the exemplary embodiments are not limited to any specific combination of hardware circuitry and/or software.

Stored on any one or a combination of computer readable media, the exemplary embodiments of the present disclosure may include software for controlling the devices and subsystems of the exemplary embodiments, for processing data and signals, for enabling the devices and subsystems of the exemplary embodiments to interact with a human user or the like. Such software can include, but is not limited to, device drivers, firmware, operating systems, development tools, applications software, and the like. Such computer-readable media further can include the computer program product of an embodiment of the present disclosure for preforming all or a portion (if processing is distributed) of the processing performed in implementations. Computer code devices of the exemplary embodiments of the present disclosure can include any suitable interpretable or executable code mechanism, including but not limited to scripts, interpretable programs, dynamic link libraries (DLLs), complete executable programs and the like.

Common forms of computer-readable media may include, for example, magnetic disks, flash memory, RAM, a PROM, an EPROM, a FLASH-EPROM, or any other suitable memory chip or medium from which a computer or processor can read.

While particular implementations and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of the present disclosure.

The term "connected", "attached", "affixed" or "coupled to" may include both direct coupling (in which two elements that are coupled to each other contact each other) and indirect coupling (in which at least one additional element is located between the two elements).

As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

The foregoing descriptions of specific embodiments of the present disclosure have been presented for purposes of illustration and description. They are not intended to be exhaustive or to limit the disclosure and method of use to the precise forms disclosed. Many modifications and variations are possible in light of the above teaching. The embodiments described were chosen and described in order to best explain the principles of the disclosure and its practical application, and to thereby enable others skilled in the art to best utilize the disclosure and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present disclosure.

The invention claimed is:

1. A system for image-based sample monitoring, the system comprising:
   a sample receiving surface comprising a well and a plurality of calibration markings, the well configured to receive a sample without undergoing one or more colorimetric reactive tests;
   an image capturing device configured to capture an image of the sample receiving surface; and
   a processing unit configured to receive the image from the image capturing device, and convert the image to usable data by comparing the sample against the plurality of calibration markings on the sample receiving surface, wherein the usable data comprises one or more of: colorimetric data, spectrophotometric data, turbidity data, dynamic light scattering data, particle size estimation, particle counting, fluorescence, phosphorescence, and reflectance data.

2. The system of claim 1, further comprising:
   a memory unit linked to electronic health records and configured to store the usable data;
   a sorting unit configured to receive the usable data from the processing unit, convert the usable data into sorted data, transform the sorted data into classified data; and determine an assessment of the sample based on the classified data; and
   a display element configured to display the assessment of the sample.

3. The system of claim 1, wherein the usable data comprises a timestamp associated with the image captured by the image capturing device.

4. The system of claim 2, wherein the sorting unit comprises one or more of: a machine learning algorithm, control charts, trends, and calibration curves.

5. The system of claim 2, wherein the sorting unit further comprises a database containing a plurality of sample data and time-dependent data, the database configured to serve as a basis of comparison for transforming the sorted data into the classified data.

6. The system of claim 1, wherein the sample is a biofluid, comprising one or more of: saliva, blood, urine, drainage fluid, plasma, wound drainage, cerebrospinal fluid, and sweat.

7. The system of claim 1, wherein the image capturing device comprises a sensor and a light source.

8. The system of claim 3, wherein the image capturing device is further configured to capture a plurality of images of the sample receiving surface at one or more predetermined time points.

9. The system of claim 1, wherein the sample receiving surface comprises an enclosure configured to be attachable to the image capturing device and provide a seal around the sample receiving surface.

10. A process for image-based sample monitoring, the process comprising:
    receiving a sample, without undergoing one or more colorimetric reactive tests, into a well on a sample receiving surface, the sample receiving surface further comprising a plurality of calibration markings;
    capturing, with an image capturing device, an image of the sample receiving surface;
    sending the image from the image capturing device to a processing unit;
    converting, with the processing unit, the image to usable data by comparing the sample against the plurality of calibration markings on the sample receiving surface, wherein the usable data comprises one or more of: colorimetric data, spectrophotometric data, turbidity data, dynamic light scattering data, particle size estimation, particle counting, fluorescence, phosphorescence, and reflectance data.

11. The process of claim 10, further comprising:
    storing the usable data in a memory unit, wherein the memory unit is linked to electronic health records;
    receiving, in a sorting unit, the usable data from the processing unit;
    converting the usable data into sorted data via the sorting unit;
    transforming the sorted data into classified data via the sorting unit;
    determining an assessment of the sample based on the classified data via the sorting unit; and
    displaying the assessment of the sample on a display element.

12. The process of claim 10, wherein the usable data comprises a timestamp associated with the image captured by the image capturing device.

13. The process of claim 11, wherein the sorting unit comprises one or more of: a machine learning algorithm, control charts, trends, and calibration curves.

14. The process of claim 11, wherein the sorting unit further comprises a database containing a plurality of sample data and time-dependent data, the database configured to serve as a basis of comparison for transforming the sorted data into the classified data.

15. The process of claim 10, wherein the sample is a biofluid, comprising one or more of: saliva, blood, urine, drainage fluid, plasma, wound drainage, cerebrospinal fluid, and sweat.

16. The process of claim 10, wherein the image capturing device comprises a sensor and a light source.

17. The process of claim 10, wherein the image capturing device is further configured to capture a plurality of images of the sample receiving surface at one or more predetermined time points.

18. The process of claim 10, wherein the sample well comprises an enclosure configured to be attachable to the image capturing device and provide a seal around the sample receiving surface.

19. The system of claim 1, wherein the sample is functionally isolated from external agents, the external agents comprising probes and reagents.

20. The process of claim 10, wherein the sample is functionally isolated from external agents, the external agents comprising probes and reagents.

\* \* \* \* \*